United States Patent
Hara et al.

(10) Patent No.: US 9,670,550 B2
(45) Date of Patent: Jun. 6, 2017

(54) METHOD FOR EXAMINATION OF CARCINOGENIC RISK

(71) Applicant: JAPANESE FOUNDATION FOR CANCER RESEARCH, Tokyo (JP)

(72) Inventors: Eiji Hara, Tokyo (JP); Naoko Ohtani, Tokyo (JP); Shin Yoshimoto, Tokyo (JP); Tze Mun Loo, Tokyo (JP)

(73) Assignee: JAPANESE FOUNDATION FOR CANCER RESEARCH, Tokyo (JP)

( * ) Notice: Subject to any disclaimer, the term of this patent is extended or adjusted under 35 U.S.C. 154(b) by 0 days.

(21) Appl. No.: 14/767,169

(22) PCT Filed: Feb. 10, 2014

(86) PCT No.: PCT/JP2014/053048
§ 371 (c)(1),
(2) Date: Aug. 11, 2015

(87) PCT Pub. No.: WO2014/126044
PCT Pub. Date: Aug. 21, 2014

(65) Prior Publication Data
US 2015/0376716 A1  Dec. 31, 2015

(30) Foreign Application Priority Data
Feb. 12, 2013 (JP) ................................. 2013-025031

(51) Int. Cl.
| | | |
|---|---|---|
| C12Q 1/68 | (2006.01) | |
| G01N 33/574 | (2006.01) | |
| A61K 31/4164 | (2006.01) | |
| A61K 31/43 | (2006.01) | |
| A61K 31/496 | (2006.01) | |
| A61K 31/7036 | (2006.01) | |
| C12Q 1/02 | (2006.01) | |

(52) U.S. Cl.
CPC ........ *C12Q 1/6886* (2013.01); *A61K 31/4164* (2013.01); *A61K 31/43* (2013.01); *A61K 31/496* (2013.01); *A61K 31/7036* (2013.01); *C12Q 1/025* (2013.01); *C12Q 1/689* (2013.01); *G01N 33/57484* (2013.01); *C12Q 2600/136* (2013.01); *C12Q 2600/158* (2013.01); *G01N 2333/33* (2013.01); *G01N 2500/10* (2013.01)

(58) Field of Classification Search
CPC .. A61K 2300/00; A61K 38/22; A61K 38/225; A61K 31/785; A61K 35/742; A61K 35/745; A61K 35/747; A61K 38/465; A61K 31/198; A61K 31/201; A61K 31/353; A61K 31/4045; A61K 31/4164; A61K 31/4184; A61K 31/43
See application file for complete search history.

(56) References Cited

U.S. PATENT DOCUMENTS 7,101,544 B1 * 9/2006 Sawada .................... A23L 2/52
424/93.51

FOREIGN PATENT DOCUMENTS

| JP | 2001-253829 | 9/2001 |
| JP | 2006-56839 | 3/2006 |
| JP | 2011-184311 | 9/2011 |
| WO | 2007/077893 | 7/2007 |
| WO | WO 2012170478 A2 * | 12/2012 |

OTHER PUBLICATIONS

Russell et al 2011(American Journal of Clinical Nutrition,(5), 1062-1072).*
Wu et al 2011 Journal of Agricultural and Food Chemistry, 59(3), 989-994.*
Yang et al Nutrition and Cancer (2005), 53(1), 117-125.*
Romond et al 1998 (Journal of Dairy Science, 81(5), 1229-1235)).*
Nagengast et al 1995 European Journal of Cancer, Part A 31A(7/8), 1067-70.*
Ou, et al 2012 Gastroenterology, (May 2012) vol. 142, No. 5, Suppl. 1, pp. S31 Conference; Abstract.*
International Search Report dated Apr. 22, 2014, Application No. PCT/JP2014/053048, English translation included.
Daikatsuji, "The encyclopedia of medicine, edition of the year 2004", Jun. 12, 2003, p. 449, partial English translation included.
Dapito, et al., "Promotion of Hepatocellular Carcinoma by the Intestinal Microbiota and TLR4", Cancer Cell, Apr. 17, 2012, pp. 504-516, vol. 21.
Yoshimoto et al., "Obesity-induced gut microbial metabolite promotes liver cancer through senescence secretome", Nature, Jul. 4, 2013, pp. 97-101, vol. 499.
Sharpless, NE and DePinho, RA, "Cancer: Crime and punishment", Nature, Aug. 4, 2005, pp. 636-637, vol. 436.
Adams, "Healing and Hurting: Molecular Mechanisms, Functions, and Pathologies of Cellular Senescence", Molecular Cell, Oct. 9, 2009, pp. 2-14, vol. 36.
Collado, M. and Serrano M., "Senescence in tumors: evidence from mice and humans", Nature Reviews Cancer, Jan. 2010, pp. 51-57, vol. 10.
Kuilman, et al., "The essence of senescence", Genes & Development, 2010, pp. 2463-2479, vol. 24.

(Continued)

*Primary Examiner* — Padma V Baskar
(74) *Attorney, Agent, or Firm* — Rankin, Hill & Clark LLP (57) ABSTRACT

The present invention provides a method capable of detecting a cancer and/or a carcinogenic risk, and a reagent for the detection thereof. The present invention also provides a method for screening for a pharmaceutical drug for reducing a carcinogenic risk and a pharmaceutical composition. Since cancer development closely correlates with alteration in gut microbiota, cancer development and/or a risk of cancer development are detected by detecting alteration in gut microbiota and a secondary bile acid produced by an intestinal bacterium. The present invention further provides a method for screening for a pharmaceutical drug with a gut microbiota as an index, and a pharmaceutical composition.

3 Claims, 7 Drawing Sheets

(56) References Cited

OTHER PUBLICATIONS

Coppe, et al., "Senescence-Associated Secretory Phenotypes Reveal Cell-Nonautonomous Functions of Oncogenic RAS and the p53 Tumor Suppressor", PLoS Biology, Dec. 2008, pp. 2853-2868, vol. 6, Issue 12.
Rodier, F. and Campisi, J., "Four faces of cellular senescence", J. Cell Biol., 2011, pp. 547-556, vol. 192, No. 4.
Kuilman, T. and Peeper, D., "Senescence-messaging secretome: SMS-ing cellular stress", Nature Reviews Cancer, Feb. 2009, pp. 81-94, vol. 9.
Ohtani, N. and Hara, E., "Roles and mechanisms of cellular senescence in regulation of tissue homeostasis", Cancer Science, May 2013, pp. 525-530, vol. 104, No. 5.
Davalos, et al., "Senescent cells as a source of inflammatory factors for tumor progression", Cancer Metastasis Rev, 2010, pp. 273-283, vol. 29.
Ohanna, et al., "Senescent cells develop a PARP-1 and nuclear factor-kB-associated secretome (PNAS)", Genes & Development, 2011, 25:1245-1261.
Nagashima, et al., "Phylogenetic Analysis of 16S Ribosomal RNA Gene Sequences from Human Fecal Microbiota and Improved Utility of Terminal Restriction Fragment Length Polymorphism Profiling", Bioscience Microflora, 2006, pp. 99-107, vol. 25.

\* cited by examiner

METHOD FOR EXAMINATION OF CARCINOGENIC RISK

TECHNICAL FIELD

The present invention provides a method of examining a cancer and/or a carcinogenic risk and a method for screening for a pharmaceutical drug.

BACKGROUND ART

Cancers are diseases caused by multiple stages of gene mutations and have been found to occur due to the damage of some genes so that cells continue to increase without limitations. In normal cells, even if genes are damaged by the stress causing DNA damage, this damage is usually repaired by a repair mechanism. However, when cells are placed under strong stress, cell death called apoptosis occurs or cell cycle halts at a cell cycle checkpoint to irreversibly terminate cell growth. This phenomenon in which cell growth is irreversibly terminated is called "senescence" and considered as an important cancer inhibition mechanism comparable to apoptosis (Non Patent Literatures 1 to 4).

Unlike apoptosis, the occurrence of senescence does not immediately induce cell death, and instead, the cells continue to survive for a long period in vivo. Recently, it has been revealed that once senescence occurs, various inflammatory cytokines are secreted in large amounts (Non Patent Literatures 5 and 6). This inflammatory cytokine secretion phenomenon associated with the senescence is called senescence-associated secretory phenotype (SASP) or senescence-messaging secretome (SMS), suggesting the possibility that this phenomenon is one of the causes of chronic inflammation or carcinogenesis based on chronic inflammation (Non Patent Literatures 5 to 7).

CITATION LIST

Non Patent Literature

Non Patent Literature 1: Sharpless N E, DePinho R A., Cancer: crime and punishment. Nature. (2005) Vol. 436 (7051): 636-7
Non Patent Literature 2: Adams P D., Healing and hurting: molecular mechanisms, functions, and pathologies of cellular senescence., Mol Cell. (2009) Vol. 36 (1): 2-14
Non Patent Literature 3: Collado M., & Serrano, M. Senescence in tumours: evidence from mice and humans., Nat Rev Cancer. (2010) Vol. 10 (1): 51-7.
Non Patent Literature 4: Kuilman, T. et al. The essence of senescence. Genes Dev. (2010) Vol. 24, 2463-2479.
Non Patent Literature 5: Coppe J. P., et al., Senescence-associated secretory phenotypes reveal cell-nonautonomous functions of oncogenic RAS and the p53 tumor suppressor., PLoS Biol. (2008) Vol. 6 (12): 2853-68.
Non Patent Literature 6: Rodier F., & Campisi, J., Four faces of cellular senescence., J Cell Biol. (2011) Vol. 192 (4): 547-56.
Non Patent Literature 7: Kuilman, T. & Peeper, D. S., Senescence-messaging secretome: SMS-ing cellular stress. (2009) Nature Rev. Cancer Vol. 9, 81-94.
Non Patent Literature 8: Ohtani N. and Hara E., Roles and mechanisms of cellular senescence in regulation of tissue homeostasis., (2013) Cancer Sci.
Non Patent Literature 9: Davalos et al., Senescent cells as a source of inflammatory factors for tumor progression., Cancer Metastasis (2010) June; 29 (2): 273-283.
Non Patent Literature 10: Ohanna et al., Senescent cells develop a PARP-1 and nuclear factor-kB-associated secretome (PNAS), Genes Dev. (2011) 25: 1245-1261.
Non Patent Literature 12: Nagashima K. et al., Phylogenetic Analysis of 16S Ribosomal RNA Gene Sequences from Human Fecal Microbiota and Improved Utility of Terminal Restriction Fragment Length Polymorphism Profiling. (2006)Bioscience and Microflora, Vol. 25, No. 3, pp. 99-107.

SUMMARY OF INVENTION

Technical Problem

However, the relation of SASP and the carcinogenic mechanism remains poorly understood. If the SASP-mediated carcinogenic mechanism is revealed, it becomes possible to detect the early stage of carcinogenesis or an individual having a high carcinogenic risk or to screen for a pharmaceutical compound on the basis of the carcinogenic mechanism.

The present inventors have produced carcinogenesis models which develop multiple liver cancer and lung cancer and analyzed the carcinogenic mechanism. As a result, the present inventors have revealed that the proportion of Gram-positive bacteria is elevated due to alteration in gut microbiota so that the concentration in blood of deoxycholic acid produced by the Gram-positive bacteria is elevated. The present inventors have further found the mechanism in which the deoxycholic acid causes the senescence of hepatic stellate cells, which in turn secrete SASP factors, thereby promoting the carcinogenesis of hepatocytes in the neighborhood thereof.

An object of the present invention is to provide an examination method leading to the detection of an individual having a high carcinogenic risk or the early detection of a cancer by detecting alteration in gut microbiota on the basis of the aforementioned elucidation of the carcinogenic mechanism. The present invention also provides a method for screening of a pharmaceutical compound with alteration in gut microbiota as an index, and a pharmaceutical composition.

Solution to Problem

The method for examining a cancer and/or a carcinogenic risk according to the present invention comprises assaying a gut microbiota and/or a product of a bacterium constituting the gut microbiota in a sample collected from a test subject.

The present inventors have analyzed carcinogenesis models and thereby revealed that cancer is developed due to alteration in gut microbiota. Thus, the carcinogenic risk can be tested by analyzing the gut microbiota.

It has been revealed that the ratio between Gram-positive bacteria and Gram-negative bacteria significantly differ, particularly, in an individual affected by a cancer or an individual having a high carcinogenic risk, as compared with normal individuals. In light of the mechanism of cancer development found by the present inventors, it has been considered that the gut microbiota is altered prior to carcinogenesis. Therefore, the carcinogenic risk can be detected prior to cancer development by analyzing the ratio between Gram-positive bacteria and Gram-negative bacteria. Since it has been revealed that, particularly, secondary bile acids produced by anaerobic bacteria induce cancers, an individual affected by a cancer or an individual having a high carcinogenic risk can be detected by detecting the anaerobic bacteria or detecting the secondary bile acids.

In the method for examining a cancer and/or a carcinogenic risk according to the present invention, the product is at least one of deoxycholic acid and lithocholic acid, which are bile acid metabolites.

The analysis of the animal models has shown the correlation between increase in bacteria producing secondary bile acids and cancer development. Furthermore, measurement of the concentration in blood of deoxycholic acid has revealed that the concentration in blood is significantly elevated in an individual affected by a cancer.

In the method for examining a cancer and/or a carcinogenic risk according to the present invention, the cancer to be tested is selected from at least one of digestive organ cancer, liver cancer, bile duct cancer, and lung cancer.

The analysis of the animal models has directly revealed alteration in gut microbiota, increase of bacteria producing secondary bile acids, and increased incidences of liver cancer and lung cancer. In light of the carcinogenic mechanism found by the present inventors, it is also evident that digestive organ cancer and bile duct cancer epidemiologically confirmed to be related to obesity can be targeted by the examining method of the present invention.

In the method for examining a cancer and/or a carcinogenic risk according to the present invention, the sample collected from a test subject is blood, saliva, an oral lavage, a gastrointestinal fluid, a gastrointestinal lavage, feces, urine, sputum, a lung lavage, or a tracheal lavage. Any sample is accepted as long as an intestinal bacterium can be detected or a metabolite from the intestinal bacterium can be assayed. The sample is preferably blood, saliva, an oral lavage, a gastrointestinal fluid, a gastrointestinal lavage, feces, urine, sputum, a lung lavage, or a tracheal lavage. This is because these samples are rich in the intestinal bacterium to be detected or its product. Particularly, feces or blood is preferred in terms of assay sensitivity and the ease of obtainment of the sample.

In the method for examining a cancer and/or a carcinogenic risk according to the present invention, the intestinal bacterium is a bacterium belonging to the genus *Clostridium*.

The analysis of the animal models has detected increase in bacterium belonging to the genus *Clostridium*, and this bacterium also includes bacteria producing deoxycholic acid. Therefore, alteration in gut microbiota can be sensitively determined by detecting a bacterium of this genus.

The test kit of a cancer and/or a carcinogenic risk according to the present invention comprises a reagent detecting at least one bacterium constituting a gut microbiota and/or a product of the bacterium constituting the gut microbiota, and further, characteristic change (oxidation, reduction, degradation, etc.) based on the metabolism of the bacterium.

The present inventors have found that alteration in gut microbiota correlates with carcinogenesis and a carcinogenic risk. Thus, any reagent detecting the alteration in gut microbiota can be used in the detection of carcinogenesis or a carcinogenic risk. For example, PCR primers recognizing a particular bacterium constituting the gut microbiota, or an antibody detecting a product of the bacterium can be used.

The method for screening for a pharmaceutical compound that reduces a carcinogenic risk according to the present invention comprises using the proliferation of a bacterium constituting a gut microbiota and/or a product of the bacterium constituting the gut microbiota as an index.

According to the carcinogenic mechanism revealed by the present inventors, alteration in gut microbiota increases a carcinogenic risk. Thus, the proliferation of a particular bacterium constituting a human gut microbiota or a metabolite produced by the intestinal bacterium can be used as an index to screen for a compound effective therefor. Since human intestinal bacteria live as indigenous bacteria in other animals, the screening can be carried out using an animal or using a bacterial culture system.

In the method for screening for a compound according to the present invention, the product of the intestinal bacterium is at least one of deoxycholic acid and lithocholic acid, which are bile acid metabolites.

The present inventors have revealed that: alteration in gut microbiota is responsible for carcinogenesis; and secondary bile acids (products of intestinal bacteria), particularly, deoxycholic acid and lithocholic acid, closely correlate with carcinogenesis. Thus, the compound can be screened for with this as an index.

In the method for screening for a compound according to the present invention, the intestinal bacterium is a bacterium belonging to the genus *Clostridium*.

Since alteration in intestinal bacterium, particularly, increase in bacterium belonging to the genus *Clostridium*, is prominent, the compound can be sensitively screened for with this as an index.

In the present invention, a compound selected from at least one of vancomycin, ampicillin, neomycin, rifampicin, a metronidazole compound, and a glycopeptide antibiotic is used in combination. The present invention also provides a method for reducing a carcinogenic risk, comprising administering a compound selected from at least one of these antibiotics.

Vancomycin, ampicillin, neomycin, rifampicin, a metronidazole compound, and a glycopeptide antibiotic have been shown to improve a condition of gut microbiota and have a carcinogenesis inhibitory effect. Thus, these antibiotics can be used in combination with other agents or administered to groups having a high carcinogenic risk, thereby improving a condition of gut microbiota and inhibiting carcinogenesis.

BRIEF DESCRIPTION OF DRAWINGS

FIGS. 1A to 1D show the preparation of carcinogenesis models with multiple cancer caused by obesity using wild-type mice, and results thereof.

FIGS. 3A to 3D show change in the rate of liver cancer development by antibiotic administration.

FIGS. 5A to 5D show the influence of deoxycholic acid on liver cancer development.

FIGS. 6A to 6B show a liver cancer induction experiment in a sterile environment.

DESCRIPTION OF EMBODIMENTS

[Method for Examining Cancer and/or Carcinogenic Risk]

The study of the present inventors on a cancer development mechanism using animal models has revealed that alteration in gut microbiota causes cancer development. Thus, a cancer and/or a carcinogenic risk can be detected with the alteration in gut microbiota as an index.

The alteration in gut microbiota occurs prior to cancer development and as such, can be detected as a carcinogenic risk before cancer development. So-called cancer markers previously put in practical use detect a cancer, whereas the present invention is very revolutionary in that a carcinogenic risk can be detected before cancer development. Specifically, the method for detecting carcinogenesis and/or a carcinogenic risk according to the present invention detects a very initial step of the carcinogenic mechanism and contributes to the early diagnosis and early detection of a cancer. As shown in Examples below, cancer development can also be detected, as a matter of course.

In addition, the present invention is very unique in that a cancer risk or cancer development can be detected from the balance among a plurality of bacteria in the gut microbiota.

(Animal Subject of Examining Method)

In this context, the test animal for the method of examining a cancer and/or a carcinogenic risk according to the present invention is not particularly limited as long as the animal whose alteration in gut microbiota is related to carcinogenesis. Examples thereof include mammals such as humans, laboratory animals (e.g., mice, rabbits, rats, guinea pigs, and monkeys), pets (e.g., dogs and cats), and livestock (e.g., goats, cattle, and sheep).

(Method for Determination)

In the case of carrying out the method for examining a cancer and/or a carcinogenic risk according to the present invention for a human, for example, the gut microbiota of the test individual is analyzed on a regular basis by medical checkup or the like. When alteration above a certain level is observed therein, the test individual can be predicted to have a cancer or to have a high carcinogenic risk. Alternatively, the range of a gut microbiota is set as to a healthy group, a high-carcinogenic risk group, and a cancer group. When the gut microbiota of the test individual falls within the range of the high-carcinogenic risk group, the test individual can be predicted to have a high carcinogenic risk; and when the gut microbiota of the test individual falls within the range of the cancer group, the test individual can be predicted to have a cancer.

Particularly, the early detection of carcinogenesis or the test of a carcinogenic risk can be conducted by applying the examining method according to the present invention to a test individual exhibiting indications pointing to alteration in gut microbiota, for example, a test individual group already diagnosed as having obesity from BMI values by medical checkup or the like. The early detection of carcinogenesis or the test of a carcinogenic risk can also be conducted by actively applying the examining method according to the present invention to a test individual indicating a high carcinogenic risk of a particular cancer, for example, a test individual exhibiting symptoms such as fatty liver, NASH (non-alcoholic steatohepatitis) as to liver cancer or a test individual smoking habitually as to lung cancer.

(Method for Detecting Gut Microbiota)

The alteration in gut microbiota can be detected from, for example, alteration in the ratio between Gram-positive bacteria and Gram-negative bacteria.

Criteria for the gut microbiota, based on which a test individual is judged as having a cancer or having a high carcinogenic risk, can be appropriately set by those skilled in the art. When the ratio of Gram-positive bacteria to Gram-negative bacteria is increased as compared with the criteria set on the basis of results of analyzing the usual gut microbiota of the individual or the gut microbiota of a healthy group, the individual may be predicted to have a cancer or to have a high carcinogenic risk.

In this context, the ratio between Gram-positive bacteria and Gram-negative bacteria may be determined by detecting any one of Gram-positive bacteria or Gram-negative bacteria. In the case of the Gram-positive bacterium, for example, a bacterium belonging to the genus *Clostridium* may be used as an index. Examples of the Gram-positive bacterium to be detected can include the genus *Clostridium* as well as the genus *Peptostreptococcus*, the genus *Eubacterium*, the genus *Staphylococcus*, the genus *Enterococcus*, the genus *Micrococcus*, the genus *Bacillus*, and the genus *Mycobacterium*.

In the case of using the bacterium belonging to the genus *Clostridium* as an index, all bacteria belonging to the genus *Clostridium* may be detected. Alternatively, one or more bacteria belonging to the genus *Clostridium* or bacteria belonging to a particular cluster of the genus *Clostridium* may be detected. Particularly, bacteria belonging to cluster XI of the genus *Clostridium* produce deoxycholic acid inducing senescence or exhibit a significantly increased ratio in carcinogenesis models. For these reasons, by bacteria belonging to cluster XI of the genus *Clostridium*, the carcinogenic risk based on the alteration in gut microbiota can probably be detected with high accuracy.

The alteration in gut microbiota can be appropriately analyzed using a reagent capable of distinguishing between Gram-positive bacteria and Gram-negative bacteria, for example, a Gram staining agent or PCR primers distinguishing between Gram-positive bacteria and Gram-negative bacteria. In the case of using PCR, primers for detection, PCR conditions, etc., can be designed and set by those skilled in the art. In the case of detecting, for example, the bacteria belonging to cluster XI of the genus *Clostridium*, primers specific for the cluster XI of the genus *Clostridium* described in Non Patent Literature 9 can also be used.

As shown in Examples, SASP is induced by deoxycholic acid through the bloodstream. SASP is found in association with senescence in various types of cells and involved in the malignant transformation of cells in their adjacent regions. Thus, an intestinal bacterium producing deoxycholic acid may be analyzed to determine the morbidity of a cancer or a carcinogenic risk. The intestinal bacterium producing deoxycholic acid is not limited to Gram-positive bacteria, and any intestinal bacterium may be to be detected as long as the bacterium has, for example, 7α-dehydrogenase, which is an enzyme that mediates the production of secondary bile acids from primary bile acids. Examples thereof include intestinal bacteria belonging to the aforementioned genus *Clostridium* (Gram-positive, anaerobic) and the genus *Bacteroides* (Gram-negative, anaerobic).

(Method for Detecting Product from Intestinal Bacterium)

The alteration in gut microbiota can also be analyzed by detecting a substance produced by an intestinal bacterium.

In the case of analyzing the ratio between Gram-positive bacteria and Gram-negative bacteria, a substance produced by a Gram-positive bacterium and a substance produced by a Gram-negative bacterium may both be detected, or any of them may be detected alone. Bacteria belonging to the genus *Clostridium*, including bacteria belonging to cluster XI of the genus *Clostridium*, for example, have 7α-dehydrogenase, which mediates the production of secondary bile acids from primary bile acids. Therefore, the secondary bile acids can be to be detected. Examples of the secondary bile acids include deoxycholic acid and lithocholic acid. Deoxycholic acid is preferably detected because the deoxycholic acid is produced by many bacteria and has a high concentration in blood or the like.

In this context, any method may be used as a method for detecting the substance produced by the intestinal bacterium as long as the method can detect the substance to be detected. Examples thereof include methods by chromatography such as gas chromatography, mass spectrometry, and detection methods using specific antibodies. Detection conditions, etc., for these detection methods can be appropriately set by those skilled in the art.

(Sample)

In the method for detecting a cancer or a carcinogenic risk according to the present invention, the sample in which the gut microbiota is analyzed is not particularly limited as long as the sample is collected from a test individual and contains an intestinal bacterium. The sample is preferably, for example, feces, urine, sputum, a gastrointestinal fluid, a gastrointestinal lavage, a lung lavage, a tracheal lavage, saliva, an oral lavage, or a biopsy sample and is more preferably feces or saliva, most preferably feces, in consideration of burdens on the test individual.

In the case of assaying the substance produced by the intestinal bacterium, the sample is not particularly limited as long as the sample is collected from a test individual and contains the substance produced by the intestinal bacterium. The sample is preferably, for example, blood, feces, urine, sputum, a gastrointestinal fluid, a gastrointestinal lavage, a lung lavage, a tracheal lavage, saliva, an oral lavage, or a biopsy sample and is more preferably feces, urine, saliva, or blood, most preferably blood, in consideration of burdens on the test individual and detection sensitivity.

(Type of Cancer)

SASP is a phenomenon found in association with senescence not only in hepatic stellate cells but in various types of cells and is known to be involved in the malignant transformation of cells in regions adjacent to the cells. The SASP phenomenon is recognized in various cells such as melanocytes, fibroblasts, and endothelial cells and in various tissues such as mammary glands, the prostate, and the skin (Non Patent Literature 9). It has been reported that SASP is also involved in the development of melanoma (Non Patent Literature 10). As shown in Examples, SASP is induced by deoxycholic acid through the bloodstream. Therefore, it can be understood that the induction of SASP also occurs in sites other than hepatic stellate cells of the liver in an individual having a high concentration in blood of a secondary bile acid such as deoxycholic acid. The carcinogenesis models used in Examples are models whose carcinogenesis was induced by obesity and a carcinogenic substance. However, any cancer can be targeted by the method for detecting a cancer and/or a carcinogenic risk according to the present invention as long as the cancer is caused by SASP triggered by alteration in gut microbiota. In fact, not only the rate of development of liver cancer whose correlation with obesity has been epidemiologically pointed out but the rate of development of lung cancer was increased in the carcinogenesis models of Example 1. Specifically, the type of the cancer targeted by the method for detecting a cancer or a carcinogenic risk according to the present invention can be any solid cancer. Among others, cancers whose correlation with obesity has been epidemiologically shown in humans, including digestive organ cancers such as esophageal cancer, stomach cancer, gallbladder cancer, liver cancer, bile duct cancer, pancreatic cancer, and colorectal cancer, and lung cancer shown to be developed at a high rate comparably with liver cancer in the carcinogenesis models can be detected particularly sensitively.

(Kit)

The test kit according to the present invention is a kit for examining the morbidity of a cancer or a carcinogenic risk in a test individual, comprising a reagent for detecting a microbiota or a substance produced by the microbiota in a sample collected from the test individual.

The kit comprises, for example, a reagent capable of distinguishing between Gram-positive bacteria and Gram-negative bacteria, for example, PCR primers capable of distinguishing between Gram-positive bacteria and Gram-negative bacteria.

In the case of using a secondary bile acid as an index, the kit can comprise, for example, an antibody detecting deoxycholic acid.

Examples of specific aspects include DNA chips equipped with primers for gene detection, protein chips with immobilized antibodies against particular bacterial proteins, and ELISA using microplates, strips, microbeads, and the like.

In the case of using a secondary bile acid as an index, the kit according to the present invention also includes, for example, sample pretreatment and extraction kits for subjecting the sample to liquid chromatography or mass spectrometry (GC/MS or LC/MS). In the case of using an antibody, an ELISA kit comprising an antibody against a bile acid-converting enzyme 7α-dehydrogenase or an antibody detecting deoxycholic acid can be provided.

The convenient DNA chip or ELISA can be used not only in a method for screening for a pharmaceutical drug candidate compound but in the monitoring of a patient having a carcinogenic risk and is thus highly useful.

[Screening Method]

On the basis of the mechanism spanning multiple stages from alteration in gut microbiota to cancer development elucidated by the present inventors, a compound having the effect of reducing a carcinogenic risk can be selected by a screening method illustrated below.

In this screening method, for example, a laboratory animal such as a mouse can be used with alteration in gut microbiota as an index, or an intestinal bacterium culture system or a cultured cell system of a carcinogenesis model can be used.

Depending on the type of the selected compound, its use can be determined. Use as a pharmaceutical compound or a food ingredient is preferred for reducing a carcinogenic risk.

The pharmaceutical compound selected by the screening method of the present invention has the effect of reducing a carcinogenic risk and can be developed as a pharmaceutical drug of a new concept leading to the prevention of the cancer.

(Screening Method using Laboratory Animal)

In a specific screening method, a laboratory animal having an altered gut microbiota is used, and a candidate substance is administered thereto for a given period. In this context, for example, the obese animal model system of Example 1 shown below can be used as the laboratory animal having an altered gut microbiota. As described in Example 1, not only a mouse but any animal usually used, such as a rat or a rabbit, can be used as long as its gut microbiota can be altered by obesity. In this context, the carcinogenesis mouse models of Examples are derived from C57BL/6, and a mouse of any strain can be used.

In this context, the cancers in the carcinogenesis models were developed using a carcinogenic substance. For merely monitoring the alteration in gut microbiota, it is not necessarily required to induce carcinogenesis.

The gut microbiota may be artificially altered, for example, by feeding an animal with a diet mixed with a particular bacterium.

A candidate substance is administered to the laboratory animal as described above for a given period, and alteration in gut microbiota is detected in the laboratory animal.

The administration of the candidate substance to the laboratory animal may be carried out by feeding the animal with a diet or drinking water mixed therewith or forcedly administering a given amount thereof using a syringe or the like.

As for the administration period, the administration can also be appropriately carried out according to the candidate substance. In the case of a substance that is secreted into mother milk, the animal may be exposed from birth to the candidate substance by mixing a diet or drinking water therewith for a mother mouse.

The method for detecting the alteration in gut microbiota can be carried out in the same way as the method for detecting the alteration in gut microbiota described about the "method for detecting a cancer or a carcinogenic risk". The ratio between Gram-positive bacteria and Gram-negative bacteria may be detected, a Gram-positive bacterium may be detected, or a secondary bile acid produced by the Gram-positive bacterium may be detected.

In this context, since the secondary bile acid produced by the intestinal bacterium is related to carcinogenesis as shown in Examples, not only the laboratory animal having a altered gut microbiota but a laboratory animal having an increased secondary bile acid concentration in blood may be used to select a compound having the effect of decreasing the secondary bile acid concentration in blood.

(Screening Method using Culture System)

A larger number of candidate substances can be screened in a short time by use of an intestinal bacterium culture system than use of the laboratory animal to efficiently select the compound of interest.

Specifically, for example, an intestinal bacterium highly correlating with a carcinogenic risk is cultured by a method well known to those skilled in the art, and each candidate substance is allowed to act thereon. Whether or not the candidate substance has the effect of reducing a carcinogenic risk can be determined with the proliferation of this intestinal bacterium as an index. When the intestinal bacterium is, for example, a bacterium increasing the carcinogenic risk, a compound inhibiting its proliferation can be selected. On the other hand, when the intestinal bacterium is a bacterium reducing the carcinogenic risk, a compound promoting its proliferation can be selected.

Alternatively, whether or not the candidate substance has the effect of reducing a carcinogenic risk can be determined with a secondary bile acid produced by the intestinal bacterium as an index. Alternatively, whether or not the candidate substance has the effect of reducing a carcinogenic risk can be determined with the secondary bile acid-producing activity of the intestinal bacterium as an index.

In addition, the candidate substances can also be screened by use of a cultured cell system of a carcinogenesis model.

Specifically, each candidate substance is added to, for example, a culture medium of cultured cells, and a secondary bile acid is allowed to act thereon to induce senescence. If the cultured cells do not exhibit senescence by the action of the secondary bile acid, the candidate substance can be judged as having the effect of inhibiting or suppressing the activity of the secondary bile acid. Thus, this candidate substance can be confirmed to have the effect of reducing a carcinogenic risk. In consideration of the accuracy of screening, the cultured cells are preferably cultured cells derived from the animal species and cancer type of an actual subject for which the carcinogenic risk is to be reduced. In this context, the presence or absence of senescence can be examined by assaying a SASP factor in the culture medium or using a well-known index for senescence, such as the presence or absence of the expression of a senescence marker.

[Pharmaceutical Composition and Treatment Method]

The compound selected by the screening method of the present invention can be used as an active ingredient in a pharmaceutical composition for the reduction of a carcinogenic risk or for the prevention of carcinogenesis.

Such a pharmaceutical composition is effective for administration to, particularly, a subject considered to have a high carcinogenic risk. The carcinogenic risk of the individual can be determined by the method for detecting a carcinogenic risk according to the present invention.

The recipient animal is not particularly limited as long as the animal is related to alteration in gut microbiota and carcinogenesis. Examples thereof include mammals such as humans, laboratory animals (e.g., mice, rabbits, rats, guinea pigs, and monkeys), pets (e.g., dogs and cats), and livestock (e.g., goats, cattle, and sheep).

As shown in Examples 3 and 4, an antibiotic, particularly, a glycopeptide antibiotic vancomycin has antibacterial properties against Gram-positive bacteria and as such, is effective for improving an intestinal environment and inhibiting carcinogenesis. Thus, the effect of reducing a carcinogenic risk can be expected by administering a glycopeptide antibiotic such as vancomycin to a patient having a high carcinogenic risk.

In this context, examples of substances that can be expected to produce effects similar to those of the glycopeptide antibiotic can include penicillin antibiotics (e.g., ampicillin), aminoglycoside antibiotics (neomycin), and rifamycin antibiotics (rifampicin). Examples of substances that can be expected to produce effects similar to those of these antibiotics can include metronidazole compounds.

EXAMPLES

Example 1

Preparation of Carcinogenesis Model with Multiple Cancer

Figure 1A:
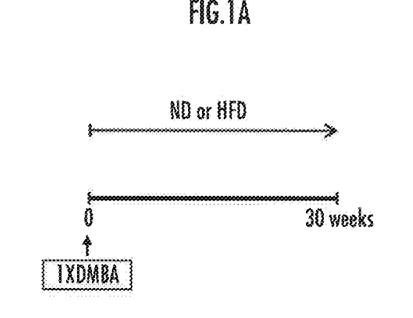
FIG. 1A schematically shows the rearing schedule of the carcinogenesis models by high-fat diet feeding.

FIG. 1A shows a method for preparing carcinogenesis models used in the present invention. An acetone solution containing 0.5% of the carcinogenic substance DMBA (7,12-dimethylberiz[a]anthracene) was applied once to the backs of wild-type (C57BL/6) neonatal mice. The neonatal mice were raised together with their mother mouse by feeding with normal diets (ND) or high-fat diet (HFD) until 4 weeks old. The high-fat diets used were D12492 (Rodent Diet with 60% kcal % Fat; Research Diets, Inc., USA). The neonatal mice were weaned at 4 weeks old and subsequently raised with normal diets or high-fat diet. At 30 weeks old, their livers and lungs were excised, and the presence or absence of cancer development was analyzed. The average body weight of the mice at the time of dissection was 33 g for the mice fed normal diets and 51 g for the mice fed high-fat diets. The mice fed high-fat diets had approximately 1.5 times the body weights of the mice fed normal diets.

Figure 1B:
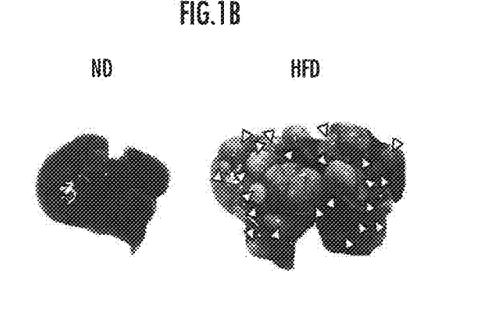
FIG. 1B shows views about the livers of mice fed normal diets (ND) or high-fat diets (HFD).

FIG. 1B shows the typical views from dissection about the livers of the mice fed normal diets or high-fat diet. The livers of the mice fed high-fat diets were enlarged into fatty livers and had multiple liver cancer (indicated by Δ).

Figure 1C:
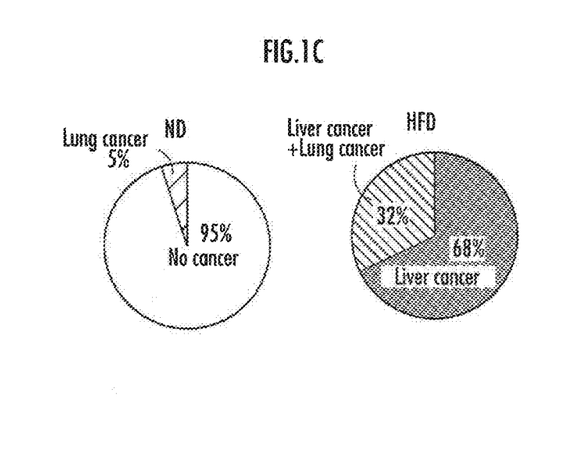
FIG. 1C shows the rate of cancer development in the mice fed normal diets or high-fat diets.

FIG. 1C shows the rate of cancer development due to the diets. In the mice fed normal diets (n=9), 5% mice developed lung cancer, whereas 95% mice showed no cancer development. By contrast, in the mice fed high-fat diets (n=18), 68% mice developed liver cancer, and 32% mice concurrently developed both liver cancer and lung cancer.

Figure 1D:
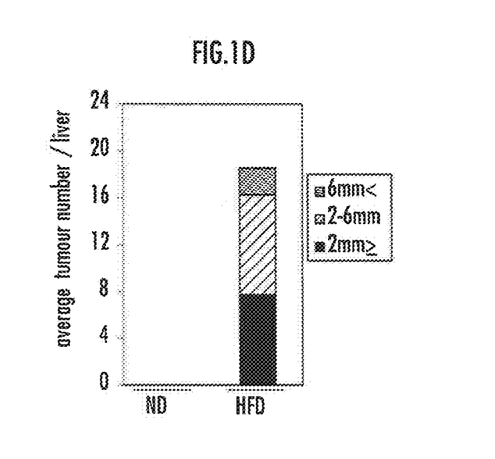
FIG. 1D shows an average tumor number in the livers and size distribution thereof.

FIG. 1D shows an average tumor number in the livers in each raised group, and size distribution thereof The group fed high-fat diets developed a large number of tumors per individual, and tumors having a size as large as 2 mm or more accounted for over half of the tumors. On the other hand, no liver cancer development was observed in the group fed normal diets.

This indicates that the mice rendered obese by high-fat diet feeding have multiple liver cancer and lung cancer. The present inventors have also obtained similar results by use of ob/ob mice known as genetically obese mice. Specifically, the ob/ob neonatal mice similarly have multiple liver cancer when treated with DMBA and then raised with normal diets.

The carcinogenesis mouse models of the present invention develop liver cancer at a rate as high as 100% rate. Thus, the carcinogenesis mouse models of the present invention can be preferably used not only in basic research but in the screening of a pharmaceutical drug. Hereinafter, the mechanism of cancer development was analyzed using the carcinogenesis mouse models.

Example 2

SASP Induction by Senescence of Hepatic Stellate Cell and Liver Cancer Development Recently, it has been suggested that some secreted factors increase a risk of cancer development, and substances classified into SASP factors are included therein (Non Patent Literature 8).

Results of previous analysis revealed that cells secreting SASP factors in the liver are hepatic stellate cells. Thus, the livers of the mice fed high-fat diets and the mice fed normal diets were subjected to cell staining to analyze whether senescence occurred in their hepatic stellate cells and SASP was observed.

Double staining was carried out using the cell marker α-smooth muscle actin for hepatic stellate cells, and p21 or p16 as the marker of inducing senescence, the foci of 53BP1 or γH2AX as the marker of involved in DNA damage response, IL-6, Gro-α, or CXCL9 as the principal SASP factor to analyze senescence and the ratio of hepatic stellate cells secreting SASP factors.

Figure 2:
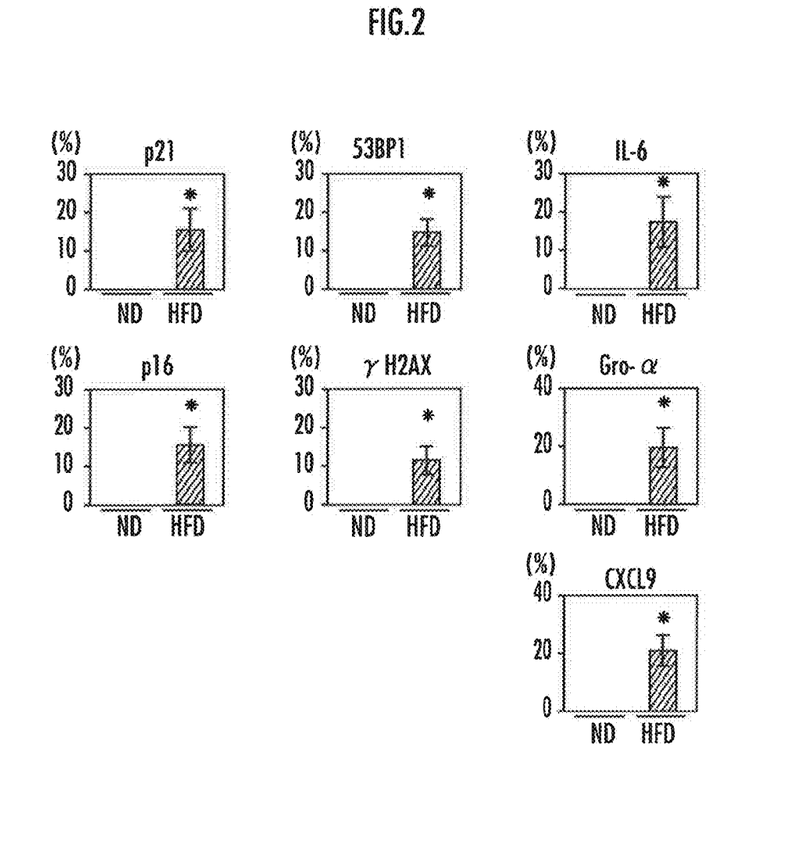
FIG. 2 shows the rates of expression of a senescence marker, a SASP-related marker, and a DNA damage marker in the hepatic stellate cells (α-smooth muscle actin-positive cells) of the mice fed normal diets or high-fat diets.

The results are shown in FIG. 2. The expression of p21 and p16 inducing senescence and the foci of 53BP1 and γH2AX involved in DNA damage response were observed in the livers of the mice fed high-fat diets, whereas the expression of these proteins was not observed in the hepatic stellate cells of the mice fed normal diets. In addition, it was shown that the senescence occur in the hepatic stellate cells of the mice fed high-fat diets and the SASP factors are secreted from the hepatic stellate cells by the expression of IL-6, Gro-α, and CXCL9.

Also, p21-p-luc mice that permitted noninvasive observation of the expression of the senescence-inducing factor $p21^{Waf1/Cip1}$ were used in the liver cancer induction experiment by high-fat diet feeding after DMBA treatment in the same way as in the carcinogenesis models of Example 1. The expression of $p21^{Waf1/Cip1}$ was observed by bioluminescence imaging.

Although the data is not shown herein, the expression of $p21^{Waf1/Cip1}$ was observed in the regions of liver cancer, showing the correlation between senescence and liver cancer development.

These results indicate that: SASP occurs by the senescence of hepatic stellate cells; and SASP is closely related to liver cancer development.

Example 3

Carcinogenesis Inhibitory Effect by Improvement of Condition in Gut Microbiota

The carcinogenesis models of the present invention were found to be mediated by SASP in association with the senescence of hepatic stellate cells.

SASP is known to occur by various causes such as the aging of individuals and oxidative stress. However, the experimental models used in the present invention are based on obesity, which differs from those previously known as causes inducing SASP. In order to analyze the cause of inducing SASP in the models of the present invention, various changes caused by obesity were analyzed. The results showed that alteration in gut microbiota correlates with SASP induction.

Figure 3:
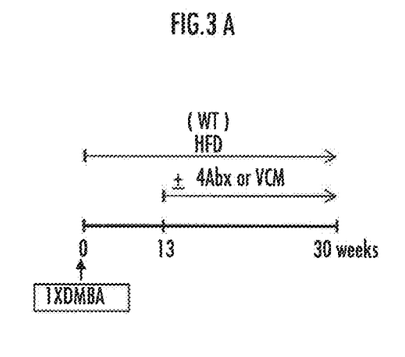
FIG. 3A schematically shows the rearing schedule of carcinogenesis models by high-fat diet feeding, wherein an antibiotic was administered to the carcinogenesis models.
FIG. 3B shows change in the level of a gene encoding bacterial 16S rRNA by antibiotic administration.
FIG. 3C shows the effect of antibiotic administration on liver cancer development and shows views about the livers of each group.
FIG. 3D shows an average tumor number in the livers and size distribution thereof.

FIG. 3A shows the experimental schedule. DMBA was applied to wild-type neonatal mice, followed by high-fat diet feeding. From 13 weeks old, an antibiotic cocktail (4Abx, antibiotic cocktail administration group) or vancomycin (VCM, vancomycin administration group) mixed with drinking water was administered to the mice. At the 30th week after the start of the raising, their livers were excised, and liver cancer development was analyzed. On the other hand, the raising of a control group was continued in the same way as the aforementioned raising up to the 13th week. The antibiotic cocktail contained ampicillin (1 g/l), neomycin (1 g/l), metronidazole (1 g/l), and vancomycin (500 mg/l). In the case of administering vancomycin alone, 500 mg/l vancomycin was administered.

FIG. 3B shows the level of a gene encoding intestinal bacterial 16s rRNA of 17 weeks after antibiotic administration, i.e., 30 weeks after birth, in each group involving 3 mice. It was shown that the amount of intestinal bacteria was completely decreased by the antibiotic cocktail and also decreased into a very small level by vancomycin.

Figure 3D:
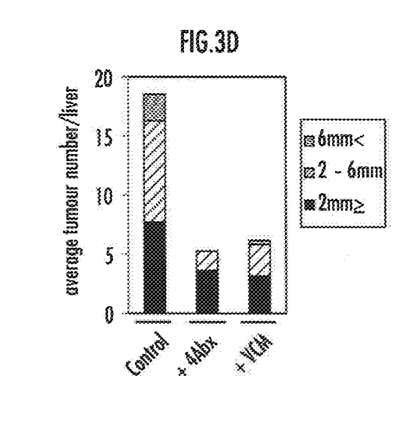

The mice of each group were dissected at the 30th week, and liver cancer development was analyzed (FIGS. 3C and 3D). Liver cancer development was observed in the control group, whereas the antibiotic cocktail administration group or the vancomycin administration group developed no liver cancer or developed liver cancer with a smaller tumor number and a smaller size as compared with the control.

These results indicate that the state of a gut microbiota before cancer development induces a cancer. Thus, if alteration in intestinal bacterium prior to liver cancer development can be determined, a risk of cancer development can be detected by this alteration as an index for the cancer development.

Example 4

Search for Intestinal Bacterium Related to Cancer Development

Figure 4:
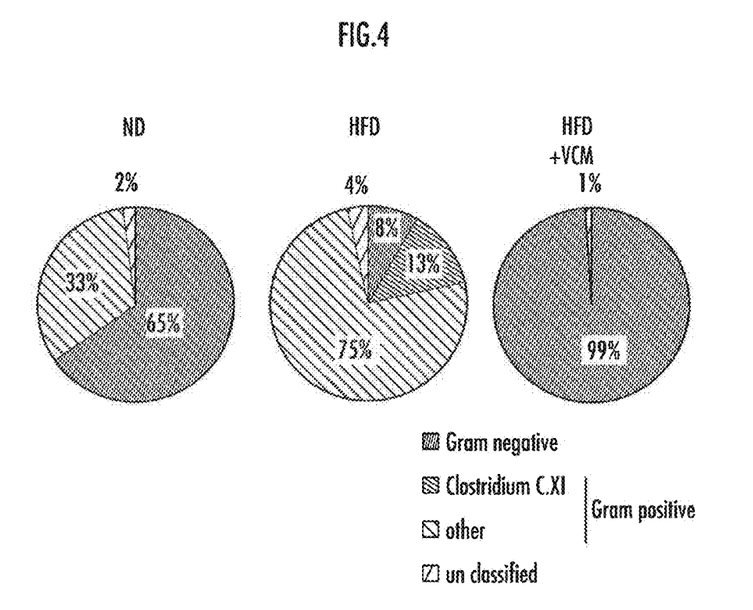
FIG. 4 shows alteration in gut microbiota by obesity.

In this Example, in order to search for an intestinal bacterium related to cancer development, how the gut microbiota was atlered was analyzed (FIG. 4). In the experimental schedule shown in FIG. 3A, 3 groups were used: a group fed normal diets, a group fed high-fat diets, and a group fed high-fat diets and also given vancomycin. At the 30th week after the start of the raising, their feces were recovered, and the gut microbiota was analyzed.

The gut microbiota was identified by PCR analysis (Non Patent Literatures 11 and 12). Specifically, DNA was extracted from the feces and purified. The gene encoding 16S rRNA in many types of bacteria was amplified by PCR using universal primers. The V1-V4 hypervariable regions were further amplified, followed by identification.

In the group fed normal diets (n=5), 54% to 79% Gram-negative bacteria and 20.9 to 45% Gram-positive bacteria (of which, cluster XI of the genus *Clostridium*: 0%) were found. In the group fed high-fat diets (n=4), 1.5 to 22% Gram-negative bacteria and 77.4 to 98.4% Gram-positive bacteria (of which, cluster XI of the genus *Clostridium*: 3.4 to 18%) were found. In the group given vancomycin (n=2), 98 to 99.8% Gram-negative bacteria and 0 to 1.9% Gram-positive bacteria (of which, cluster XI of the genus *Clostridium*: 0%) were found.

The average values of these ratios are shown in FIG. 4. The mouse group fed normal diets (ND) contained 65% Gram-negative bacteria on average, whereas the Gram-negative bacteria were significantly decreased to 8% on average in the mouse group fed high-fat diets (HFD) which instead contained 88% Gram-positive bacteria on average.

Among the Gram-positive bacteria, cluster XI of the genus *Clostridium* accounted for a very large proportion (13% on average).

In the mouse group fed high-fat diets and also given vancomycin (HFD+VCM), Gram-negative microbiota accounted for the substantial proportion (99% on average).

Such alteration in gut microbiota was compared with cancer development, showing that the increased ratio of Gram-positive bacteria correlates with an increased risk of liver cancer development. In addition, it was shown that the increased ratio of bacteria of cluster XI of the genus *Clostridium* correlates with an increased risk of liver cancer development.

Thus, a risk of liver cancer development can be tested on the basis of the increased ratio of Gram-positive bacteria by analyzing the ratio between Gram-negative bacteria and Gram-positive bacteria in the gut microbiota. Also, a risk of liver cancer development can be tested by detecting intestinal cluster XI of the genus *Clostridium*.

Although these results were obtained using the mouse models, for humans, a gut microbiota correlating with cancer development can also be identified by a similar approach. Also, a risk of cancer development can be tested by detecting the ratio between Gram-negative bacteria and Gram-positive bacteria or a particular bacterium correlating with identified cancer development.

Example 5

Induction of Carcinogenesis Mediated through SASP by Deoxycholic Acid

Since the bacteria of the cluster XI of the genus *Clostridium* produces secondary bile acids, the relation of the secondary bile acids to liver cancer development was analyzed.

Figure 5A:
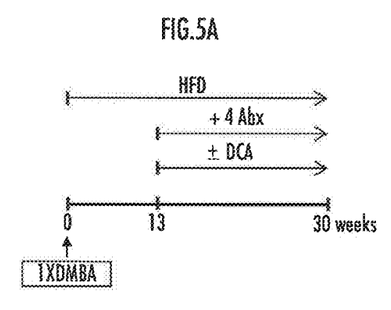
FIG. 5A schematically shows the rearing schedule of mice fed high-fat diets and given an antibiotic cocktail, wherein deoxycholic acid was administered to the mice.

From the 13th week after the start of the raising, the antibiotic cocktail was administered to mice fed high-fat diets, which were then further raised. To these mice, 40 μg/g body weight of deoxycholic acid (DCA) or only a vehicle as a control was orally administered three times a week (FIG. 5A).

Figure 5B:
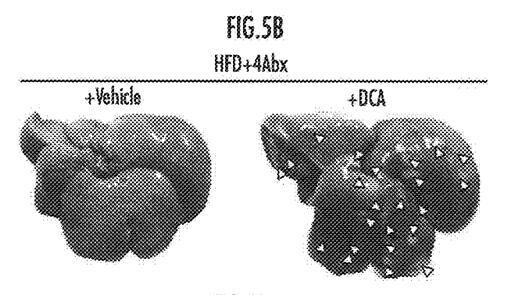
FIG. 5B shows views about the livers of a control group (high-fat diet+antibiotic cocktail administration) and a deoxycholic acid administration group (high-fat diet+antibiotic cocktail administration+deoxycholic acid administration).
Figure 5C:
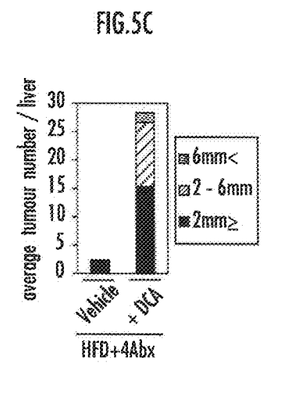
FIG. 5C shows an average tumor number in the livers of each group and size distribution thereof.

FIG. 5B shows typical views about the livers of both groups. The mice given deoxycholic acid developed a large number of liver tumors (indicated by Δ in the diagram), whereas cancer development was rarely seen in the control mouse group given only the vehicle. FIG. 5C shows an average tumor number per liver of an individual, and the size thereof (n=3). The cancer was rarely developed in the control mouse group given only the vehicle, and even if the cancer was developed, its tumor size was small. On the other hand, the deoxycholic acid administration group had multiple cancer (25 or more tumors per individual), and also, its size was large.

The aforementioned analysis showed that deoxycholic acid causes liver cancer development.

The deoxycholic acid in the blood of these mice was assayed. As a result, the mice fed high-fat diets had 3 times more concentrations of deoxycholic acid than that of the mice fed normal diets, whereas deoxycholic acid was detected at a level below the limit in the mice fed high-fat diets and also given the antibiotic cocktail.

Thus, it can be predicted that a carcinogenic risk is increased even if the deoxycholic acid concentration in blood is a few times that of healthy subjects.

Although the data is not shown herein, cultured hepatic stellate cells were cultured in a 10% Dulbecco's modified Eagle's medium (supplemented with 10% FBS, 3% $O_2$, 5% $CO_2$), and 200 μM of deoxycholic acid was added thereto. As a result, increase in reactive oxygen species (ROS) causing senescence or the expression of SASP-related factors was confirmed. This implies that a carcinogenic risk is increased even if the secondary bile acids typified by deoxycholic acid have a very low concentration.

It was further confirmed using an immunostaining method that deoxycholic acid delivered to the liver induces SASP in hepatic stellate cells.

Figure 5D:
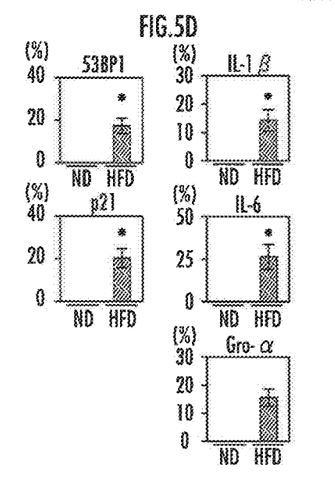
FIG. 5D shows the rates of expression of a senescence marker, a SASP-related marker, and a DNA damage marker in the hepatic stellate cells (α-smooth muscle actin-positive cells) of the mice given deoxycholic acid.

As shown in FIG. 5D, p21 known to induce SASP and the SASP factors IL-1β, IL-6, and Gro-α were expressed in the deoxycholic acid administration group, whereas no expression thereof was confirmed in the control group.

Example 6

Carcinogenic Risk Based on Presence or Absence of Gut Microbiota

As shown in Examples 3 and 4, a risk of liver carcinogenesis was found to be reduced by decreasing the number of intestinal bacteria by antibiotic administration. Thus, mice were raised in a sterile environment carrying no intestinal bacterium, and neonatal mice were treated with DMBA and raised with high-fat diets in the same way as in Example 1. At the age of 30 weeks, the presence or absence of liver cancer development was analyzed in obese mice whose body weight reached 45 g or more.

Since germ-free mice were less likely to be obese because of the absence of intestinal bacteria, as compared with mice having indigenous bacteria (average body weight: approximately 57 g), and had an average body weight of approximately 48 g.

Figure 6A:
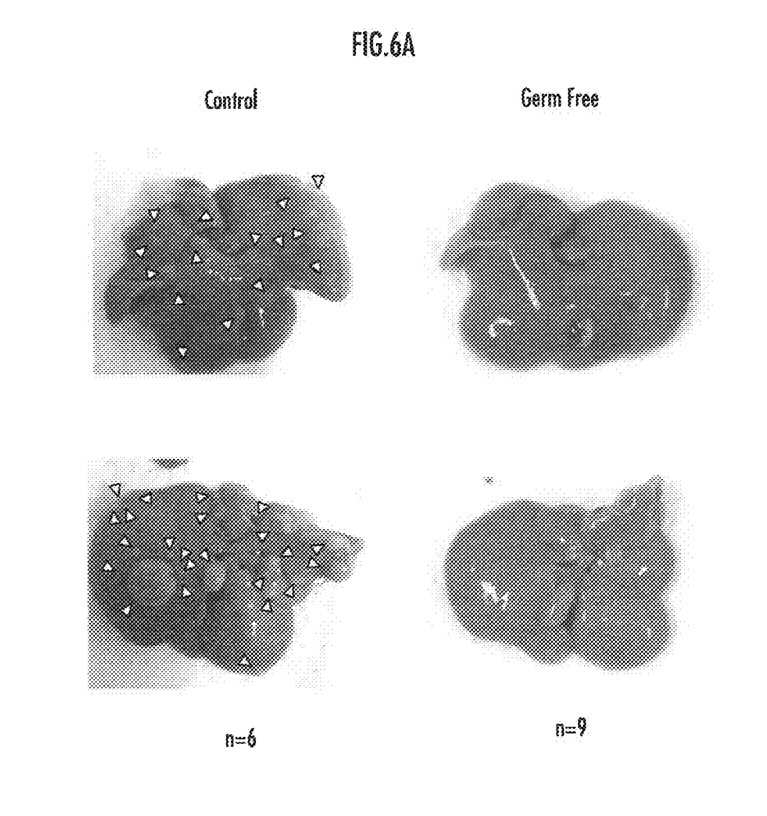
FIG. 6A shows views about the livers of germ-free mice carrying no intestinal bacterium (Germ Free) and mice carrying indigenous bacteria (Control) at the age of 30 weeks, wherein the mice were treated with DMBA and then raised by high-fat diet feeding.
Figure 6B:
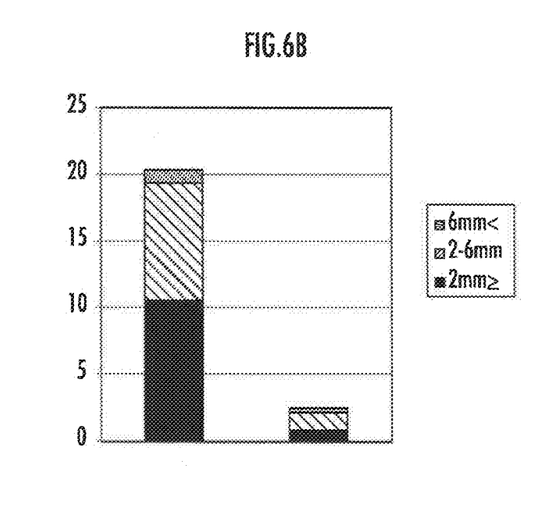
FIG. 6B shows an average tumor number in the livers and size distribution thereof.

FIG. 6A shows typical views about the livers of mice in each group. In FIG. 6A, liver cancer is indicated by Δ. FIG. 6B shows an average tumor number per liver of an individual, and the size thereof An average value from 6 individuals for the control mice and 9 individuals for the germ-free mice are shown.

Liver cancer development was seen in the mice having indigenous bacteria (control mice), whereas cancer development was inhibited in the germ-free mice, albeit obese, carrying no gut microbiota.

The results about the germ-free mice, albeit obese, having a low risk of liver cancer development indicate that the presence or absence of intestinal bacteria correlates with liver cancer development. In consideration of the results of Example 5, the intestinal bacteria are found to produce secondary bile acids and be deeply involved in liver cancer development.

Figure 7:
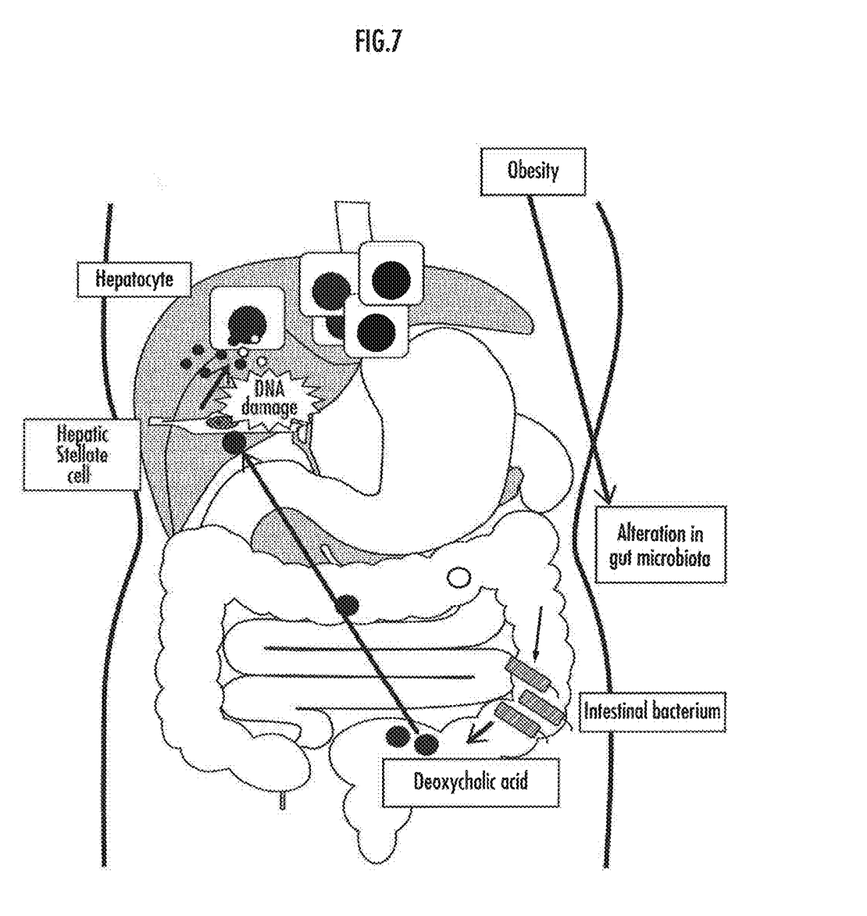
FIG. 7 schematically shows the mechanism under which alteration in gut microbiota occurs due to obesity to develop liver cancer.

The results of Examples 2 to 6 suggest that the following mechanism works in cancer development (FIG. 7). Alteration in gut microbiota, particularly, increase in deoxycholic acid-producing intestinal bacterium belonging to cluster XI of the genus *Clostridium*, takes place, resulting in the elevated concentration of deoxycholic acid in blood. In the case of liver cancer, the deoxycholic acid is delivered to the liver through enterohepatic circulation to cause the senescence of hepatic stellate cells. The senescent hepatic stellate cells secrete SASP factors. This SASP induces the cell growth of hepatocytes in the neighborhood of the hepatic stellate cells, leading to liver cancer development.

According to the present invention, alteration in gut microbiota occurs prior to cancer development. Therefore, a risk of cancer development can be tested by determining the alteration in gut microbiota. The alteration in gut microbiota may be examined as the balance between Gram-negative bacteria and Gram-positive bacteria or may be tested by detecting a secondary bile acid.

Also, a compound inhibiting liver cancer development can be searched for by using the mouse models of Examples and further administering a candidate compound. Thus, a novel pharmaceutical compound can also be screened for.

The method for screening for a pharmaceutical compound according to the present invention is also effective for a developed cancer and may further select a compound for use as a pharmaceutical drug reducing a carcinogenic risk.

Specifically, in the present invention, it was shown that carcinogenesis is inhibited by improving the condition of gut microbiota. Thus, the screening method can search for a compound that is a pharmaceutical drug reducing a carcinogenic risk.

Particularly, the possibility was shown that alteration in gut microbiota induces digestive organ cancer, liver cancer, bile duct cancer, or lung cancer. Therefore, a pharmaceutical drug administrable to patients with these diseases or individuals having a risk of these diseases can be screened for.

The invention claimed is:

1. A method for screening whether a test subject has a liver cancer and/or an increased risk of liver cancer, comprising: assaying gut microbiota in a sample collected from the test subject; and determining whether a ratio of Gram-positive bacteria to Gram-negative bacteria in the assayed sample collected from the test subject exceeds a range of ratios of Gram-positive bacteria to Gram-negative bacteria in gut microbiota in samples collected from a healthy group.

2. The method according to claim 1, wherein the sample collected from the test subject is saliva, an oral lavage, a gastrointestinal fluid, a gastrointestinal lavage, and sputum.

3. The method according to claim 1, wherein
   the gut microbiota of the test subject is assayed on a regular basis, and
   an increase in the ratio of Gram-positive bacteria to Gram-negative bacteria for the test subject indicates an increased risk of cancer.

* * * * *